(12) United States Patent
Olsen

(10) Patent No.: US 9,320,869 B2
(45) Date of Patent: Apr. 26, 2016

(54) APPARATUS FOR MAKING A CATHETER

(71) Applicant: UnoMedical A/S, Birkeroed (DK)

(72) Inventor: Jan Kent Olsen, Hillerod (DK)

(73) Assignee: UNOMEDICAL A/S, Birkeroed (DK)

( * ) Notice: Subject to any disclaimer, the term of this patent is extended or adjusted under 35 U.S.C. 154(b) by 0 days.

(21) Appl. No.: 14/879,811

(22) Filed: Oct. 9, 2015

(65) Prior Publication Data

US 2016/0030706 A1 Feb. 4, 2016

Related U.S. Application Data

(62) Division of application No. 12/665,278, filed as application No. PCT/EP2008/054549 on Apr. 15, 2008, now Pat. No. 9,186,480.

(60) Provisional application No. 60/946,655, filed on Jun. 27, 2007.

(30) Foreign Application Priority Data

Jun. 20, 2007 (EP) .................................. 07012017

(51) Int. Cl.
*B29C 57/04* (2006.01)
*A61M 25/00* (2006.01)
*B26F 1/00* (2006.01)

(52) U.S. Cl.
CPC .......... *A61M 25/0015* (2013.01); *B26F 1/0015* (2013.01)

(58) Field of Classification Search
CPC .......... A61M 25/0015; A61M 25/001; A61M 25/0017

USPC ..................... 264/68, 154, 155, 156
See application file for complete search history.

(56) References Cited

U.S. PATENT DOCUMENTS

| 1,592,462 A | 7/1926 | MacGregor |
| 2,047,010 A | 7/1936 | Dickinson |

(Continued)

FOREIGN PATENT DOCUMENTS

| DE | 4342329 A1 | 6/1994 |
| DE | 19631921 A1 | 3/1997 |

(Continued)

OTHER PUBLICATIONS

PCT/EP2008/054549 International Preliminary Report on Patentability completed Sep. 23, 2009.

(Continued)

*Primary Examiner* — Joseph S Del Sole
*Assistant Examiner* — Thukhanh T Nguyen
(74) *Attorney, Agent, or Firm* — Wilson Sonsini Goodrich & Rosati

(57) ABSTRACT

The present invention concerns a catheter for medical purposes, such as for insertion into a body opening for draining fluids, wherein the catheter comprises a flexible tube having a distal end region wherein the tube is provided with at least one draining opening, characterised in that the peripheral edge on the outside of the tube is provided with a curvature for creating a smooth transition between the exterior surface of the tube and the substantially radially oriented cut constituting the opening side and wherein said curvature is a rounded edge with a curvature radius between 0.2-0.6 mm. The invention further concerns a method of making such catheter and an apparatus for performing this method.

7 Claims, 8 Drawing Sheets

(56) References Cited

U.S. PATENT DOCUMENTS

| | | | |
|---|---|---|---|
| 2,295,849 A | 9/1942 | Kayden |
| 2,690,529 A | 9/1954 | Lindblad |
| 2,972,779 A | 2/1961 | Cowley |
| 3,059,802 A | 10/1962 | Mitchell |
| 3,074,541 A | 1/1963 | Roehr |
| 3,149,186 A | 9/1964 | Coanda |
| 3,221,739 A | 12/1965 | Rosenthal |
| 3,221,740 A | 12/1965 | Rosenthal |
| 3,306,291 A | 2/1967 | Burke |
| 3,485,352 A | 12/1969 | Nicholas |
| 3,509,879 A | 5/1970 | Louis et al. |
| 3,519,158 A | 7/1970 | Douglas |
| 3,547,119 A | 12/1970 | Hall et al. |
| 3,575,337 A | 4/1971 | Bernhardt |
| 3,610,240 A | 10/1971 | Harautuneian |
| 3,615,039 A | 10/1971 | Ward |
| 3,670,727 A | 6/1972 | Reiterman |
| 3,783,895 A | 1/1974 | Weichselbaum |
| 3,788,374 A | 1/1974 | Saijo |
| 3,810,469 A | 5/1974 | Hurschman |
| 3,835,862 A | 9/1974 | Villari |
| 3,840,011 A | 10/1974 | Wright |
| 3,893,448 A | 7/1975 | Brantigan |
| 3,937,219 A | 2/1976 | Karakashian |
| 3,986,507 A | 10/1976 | Watt |
| 3,986,508 A | 10/1976 | Barrington |
| 3,995,518 A | 12/1976 | Spiroff |
| 4,022,205 A | 5/1977 | Tenczar |
| 4,111,029 A | 9/1978 | Dulaquais |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,296,786 A | 10/1981 | Brignola |
| D267,199 S | 12/1982 | Koenig |
| 4,402,407 A | 9/1983 | Maly |
| 4,415,393 A | 11/1983 | Grimes |
| 4,508,367 A | 4/1985 | Oreopoulos et al. |
| 4,543,088 A | 9/1985 | Bootman et al. |
| 4,617,019 A | 10/1986 | Fecht et al. |
| RE32,922 E | 5/1989 | Levin et al. |
| 4,956,989 A | 9/1990 | Nakajima |
| 4,970,954 A | 11/1990 | Weir et al. |
| 5,011,475 A | 4/1991 | Olson |
| 5,020,665 A | 6/1991 | Bruno |
| 5,024,662 A | 6/1991 | Menes et al. |
| 5,067,496 A | 11/1991 | Eisele |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van Den Haak |
| 5,116,325 A | 5/1992 | Paterson |
| 5,121,751 A | 6/1992 | Panalletta |
| 5,129,884 A | 7/1992 | Dysarz |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,375 A | 9/1992 | Sullivan et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,248,301 A | 9/1993 | Koenig, Jr. et al. |
| 5,256,149 A | 10/1993 | Banik et al. |
| 5,256,152 A | 10/1993 | Marks |
| 5,257,980 A | 11/1993 | Van Antwerp et al. |
| 5,267,963 A | 12/1993 | Bachynsky |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,344,007 A | 9/1994 | Nakamura et al. |
| 5,350,392 A | 9/1994 | Purcell et al. |
| 5,354,280 A | 10/1994 | Haber et al. |
| 5,354,337 A | 10/1994 | Hoy |
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,379,895 A | 1/1995 | Foslien |
| 5,384,174 A | 1/1995 | Ward et al. |
| 5,387,197 A | 2/1995 | Smith et al. |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,425,715 A | 6/1995 | Dalling et al. |
| 5,429,607 A | 7/1995 | McPhee |
| 5,429,613 A | 7/1995 | D'Amico |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,478,316 A | 12/1995 | Bitdinger et al. |
| 5,490,841 A | 2/1996 | Landis |
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,520,654 A | 5/1996 | Wahlberg |
| 5,522,803 A | 6/1996 | Teissen-Simony |
| 5,527,287 A | 6/1996 | Miskinyar |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,549,577 A | 8/1996 | Siegel et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili et al. |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall et al. |
| 5,643,216 A | 7/1997 | White |
| 5,643,220 A | 7/1997 | Cosme |
| 5,658,256 A | 8/1997 | Shields |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,697,907 A | 12/1997 | Gaba |
| 5,700,250 A | 12/1997 | Erskine |
| 5,702,371 A | 12/1997 | Bierman |
| 5,704,920 A | 1/1998 | Gyure |
| 5,709,662 A | 1/1998 | Olive et al. |
| 5,714,225 A | 2/1998 | Hansen et al. |
| 5,738,641 A | 4/1998 | Watson et al. |
| 5,741,288 A | 4/1998 | Rife |

(56) References Cited

U.S. PATENT DOCUMENTS

| | | |
|---|---|---|
| 5,752,923 A | 5/1998 | Terwilliger |
| 5,807,316 A | 9/1998 | Teeple, Jr. |
| 5,807,348 A | 9/1998 | Zinger et al. |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| 5,843,001 A | 12/1998 | Goldenberg |
| 5,848,990 A | 12/1998 | Cirelli et al. |
| 5,851,197 A | 12/1998 | Marano et al. |
| 5,858,001 A | 1/1999 | Tsals et al. |
| 5,865,806 A | 2/1999 | Howell |
| 5,899,886 A | 5/1999 | Cosme |
| 5,911,705 A | 6/1999 | Howell |
| 5,913,846 A | 6/1999 | Szabo |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,935,109 A | 8/1999 | Donnan |
| 5,947,931 A | 9/1999 | Bierman |
| 5,947,935 A | 9/1999 | Rhinehart et al. |
| 5,951,523 A | 9/1999 | Osterlind et al. |
| 5,954,643 A | 9/1999 | VanAntwerp et al. |
| 5,957,892 A | 9/1999 | Thorne |
| 5,957,897 A | 9/1999 | Jeffrey |
| 5,968,011 A | 10/1999 | Larsen et al. |
| 5,971,966 A | 10/1999 | Lav |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Petersen et al. |
| D417,733 S | 12/1999 | Howell et al. |
| 6,017,328 A | 1/2000 | Fischell et al. |
| 6,017,598 A | 1/2000 | Kreischer et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,079,432 A | 6/2000 | Paradis |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stradella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. et al. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,283,744 B1 | 9/2001 | Edmondson et al. |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,364,113 B1 | 4/2002 | Faasse, Jr. et al. |
| 6,378,218 B1 | 4/2002 | Sigwart et al. |
| 6,379,335 B1 | 4/2002 | Rigon et al. |
| 6,387,076 B1 | 5/2002 | Landuyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | Roenborg et al. |
| 6,450,992 B1 | 9/2002 | Cassidy, Jr. |
| 6,485,461 B1 | 11/2002 | Mason et al. |
| 6,488,663 B1 | 12/2002 | Steg |
| 6,503,222 B2 | 1/2003 | Lo |
| 6,517,517 B1 | 2/2003 | Farrugia et al. |
| 6,520,938 B1 | 2/2003 | Funderburk et al. |
| D472,316 S | 3/2003 | Douglas et al. |
| 6,530,256 B1 | 3/2003 | Irie et al. |
| D472,630 S | 4/2003 | Douglas et al. |
| 6,572,586 B1 | 6/2003 | Wojcik |
| 6,579,267 B2 | 6/2003 | Lynch et al. |
| 6,582,397 B2 | 6/2003 | Alesi et al. |
| 6,595,962 B1 | 7/2003 | Perthu |
| 6,607,509 B2 | 8/2003 | Bobroff et al. |
| 6,607,511 B2 | 8/2003 | Halseth et al. |
| 6,613,064 B2 | 9/2003 | Rutynowski et al. |
| 6,620,133 B1 | 9/2003 | Steck |
| 6,620,136 B1 | 9/2003 | Pressly, Sr. et al. |
| 6,620,140 B1 | 9/2003 | Metzger |
| 6,629,949 B1 | 10/2003 | Douglas |
| 6,645,182 B1 | 11/2003 | Szabo |
| 6,659,982 B2 | 12/2003 | Douglas et al. |
| 6,685,674 B2 | 2/2004 | Douglas et al. |
| 6,699,218 B2 | 3/2004 | Flaherty et al. |
| 6,702,779 B2 | 3/2004 | Connelly et al. |
| 6,726,649 B2 | 4/2004 | Swenson et al. |
| 6,736,797 B1 | 5/2004 | Larsen et al. |
| 6,743,203 B1 | 6/2004 | Pickhard |
| 6,749,587 B2 | 6/2004 | Flaherty |
| 6,749,589 B1 | 6/2004 | Douglas et al. |
| 6,755,805 B1 | 6/2004 | Reid |
| 6,776,775 B1 | 8/2004 | Mohammad |
| 6,790,199 B1 | 9/2004 | Gianakos |
| 6,805,686 B1 | 10/2004 | Fathallah et al. |
| 6,808,506 B2 | 10/2004 | Lastovich et al. |
| 6,811,545 B2 | 11/2004 | Vaillancourt |
| 6,814,720 B2 | 11/2004 | Olsen et al. |
| 6,824,530 B2 | 11/2004 | Wagner et al. |
| 6,824,531 B1 | 11/2004 | Zecha, Jr. et al. |
| 6,830,562 B2 | 12/2004 | Mogensen et al. |
| 6,837,877 B2 | 1/2005 | Zurcher et al. |
| 6,837,878 B2 | 1/2005 | Smutney et al. |
| 6,840,922 B2 | 1/2005 | Nielsen et al. |
| 6,880,701 B2 | 4/2005 | Bergeron et al. |
| 6,923,791 B2 | 8/2005 | Douglas |
| 6,926,694 B2 | 8/2005 | Marano-Ford et al. |
| 6,939,324 B2 | 9/2005 | Gonnelli et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkinson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| 7,083,592 B2 | 8/2006 | Lastovich et al. |

(56) References Cited

U.S. PATENT DOCUMENTS

| | | |
|---|---|---|
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkinson et al. |
| 7,115,112 B2 | 10/2006 | Mogensen et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| 7,303,543 B1 | 12/2007 | Maule et al. |
| 7,309,326 B2 | 12/2007 | Fangrow, Jr. |
| 7,322,473 B2 | 1/2008 | Fux |
| 7,407,491 B2 | 8/2008 | Fangrow, Jr. |
| 7,407,493 B2 | 8/2008 | Cane et al. |
| 7,431,876 B2 | 10/2008 | Mejlhede et al. |
| 7,441,655 B1 | 10/2008 | Hoftman |
| 7,569,262 B2 | 8/2009 | Szabo et al. |
| 7,648,494 B2 | 1/2010 | Kornerup et al. |
| 7,766,867 B2 | 8/2010 | Lynch et al. |
| 7,846,132 B2 | 12/2010 | Gravesen et al. |
| 7,850,652 B2 | 12/2010 | Liniger et al. |
| 8,012,126 B2 | 9/2011 | Tipsmark et al. |
| 8,087,333 B2 | 1/2012 | Oishi |
| 8,123,724 B2 | 2/2012 | Gillespie, III |
| 8,303,549 B2 | 11/2012 | Mejlhede et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer et al. |
| 2001/0053889 A1 | 12/2001 | Marggi et al. |
| 2001/0056284 A1 | 12/2001 | Purcell et al. |
| 2002/0022798 A1 | 2/2002 | Connelly et al. |
| 2002/0022855 A1 | 2/2002 | Bobroff et al. |
| 2002/0026152 A1 | 2/2002 | Bierman |
| 2002/0055711 A1 | 5/2002 | Lavi et al. |
| 2002/0068904 A1 | 6/2002 | Bierman et al. |
| 2002/0072720 A1 | 6/2002 | Hague et al. |
| 2002/0074345 A1 | 6/2002 | Schneider et al. |
| 2002/0077599 A1 | 6/2002 | Wojcik |
| 2002/0082543 A1 | 6/2002 | Park et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Ackley et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel et al. |
| 2004/0162521 A1 | 8/2004 | Bengtsson |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia et al. |
| 2004/0236284 A1 | 11/2004 | Hoste et al. |
| 2004/0243065 A1 | 12/2004 | McConnell et al. |
| 2005/0080386 A1 | 4/2005 | Reid |
| 2005/0101912 A1 | 5/2005 | Faust et al. |
| 2005/0119611 A1 | 6/2005 | Marano-Ford et al. |
| 2005/0119619 A1 | 6/2005 | Haining |
| 2005/0124936 A1 | 6/2005 | Mogensen et al. |
| 2005/0131347 A1 | 6/2005 | Marano-Ford et al. |
| 2005/0165382 A1 | 7/2005 | Fulford |
| 2005/0192560 A1 | 9/2005 | Walls et al. |
| 2005/0240154 A1 | 10/2005 | Mogensen et al. |
| 2005/0256456 A1 | 11/2005 | Marano-Ford et al. |
| 2005/0261629 A1 | 11/2005 | Marano-Ford et al. |
| 2006/0036214 A1 | 2/2006 | Mogensen et al. |
| 2006/0041224 A1 | 2/2006 | Jensen |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld |
| 2006/0142698 A1 | 6/2006 | Ethelfeld |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney et al. |
| 2006/0184140 A1 | 8/2006 | Okiyama |
| 2006/0200073 A1 | 9/2006 | Radmer et al. |
| 2006/0241551 A1 | 10/2006 | Lynch et al. |
| 2006/0247553 A1 | 11/2006 | Diermann et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1 | 11/2006 | Nielsen et al. |
| 2006/0264890 A1 | 11/2006 | Moberg et al. |
| 2007/0005017 A1 | 1/2007 | Alchas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049865 A1 | 3/2007 | Radmer et al. |
| 2007/0049870 A1 | 3/2007 | Gray et al. |
| 2007/0051784 A1 | 3/2007 | Money et al. |
| 2007/0066955 A1 | 3/2007 | Sparholt et al. |
| 2007/0088271 A1 | 4/2007 | Richards |
| 2007/0093754 A1 | 4/2007 | Mogensen et al. |
| 2007/0104596 A1 | 5/2007 | Preuthun et al. |
| 2007/0112301 A1 | 5/2007 | Preuthun et al. |
| 2007/0112303 A1 | 5/2007 | Liniger |
| 2007/0129688 A1 | 6/2007 | Scheurer et al. |
| 2007/0173767 A1 | 7/2007 | Lynch et al. |
| 2007/0179444 A1 | 8/2007 | Causey et al. |
| 2007/0185441 A1 | 8/2007 | Fangrow |
| 2007/0191772 A1 | 8/2007 | Wojcik |
| 2007/0191773 A1 | 8/2007 | Wojcik |
| 2007/0203454 A1 | 8/2007 | Shermer et al. |
| 2007/0213673 A1 | 9/2007 | Douglas |
| 2007/0244448 A1 | 10/2007 | Lastovich et al. |
| 2007/0299409 A1 | 12/2007 | Whitbourne et al. |
| 2008/0269687 A1 | 10/2008 | Chong et al. |
| 2008/0312601 A1 | 12/2008 | Cane |

(56) References Cited

U.S. PATENT DOCUMENTS

| | | |
|---|---|---|
| 2009/0062767 A1 | 3/2009 | Van et al. |
| 2009/0326456 A1 | 12/2009 | Cross et al. |
| 2010/0004597 A1 | 1/2010 | Gyrn et al. |
| 2010/0137829 A1 | 6/2010 | Nielsen et al. |
| 2010/0228226 A1 | 9/2010 | Nielsen |

FOREIGN PATENT DOCUMENTS

| | | |
|---|---|---|
| DE | 29905072 U1 | 9/1999 |
| DE | 10117285 A1 | 11/2002 |
| DE | 20320207 U1 | 10/2004 |
| EP | 0272530 A2 | 6/1988 |
| EP | 0117632 B1 | 8/1989 |
| EP | 0239244 B1 | 9/1991 |
| EP | 0451040 A1 | 10/1991 |
| EP | 0615768 A2 | 9/1994 |
| EP | 0652027 A1 | 5/1995 |
| EP | 0657184 A1 | 6/1995 |
| EP | 0744183 A2 | 11/1996 |
| EP | 0799626 A1 | 10/1997 |
| EP | 0544837 B1 | 11/1997 |
| EP | 0688232 B1 | 12/1998 |
| EP | 0937475 A2 | 8/1999 |
| EP | 0651662 B1 | 9/1999 |
| EP | 0956879 A1 | 11/1999 |
| EP | 1086718 A1 | 3/2001 |
| EP | 1125593 A1 | 8/2001 |
| EP | 0775501 B1 | 6/2002 |
| EP | 0714631 B1 | 12/2002 |
| EP | 1350537 A1 | 10/2003 |
| EP | 1360970 A1 | 11/2003 |
| EP | 1380315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1329233 B1 | 9/2004 |
| EP | 1475113 A1 | 11/2004 |
| EP | 1495775 A1 | 1/2005 |
| EP | 1502613 A1 | 2/2005 |
| EP | 1525873 A1 | 4/2005 |
| EP | 1527792 A1 | 5/2005 |
| EP | 1559442 A2 | 8/2005 |
| EP | 1616594 A1 | 1/2006 |
| EP | 1704889 A1 | 9/2006 |
| EP | 1719537 A2 | 11/2006 |
| EP | 1762259 A1 | 3/2007 |
| EP | 1764125 A1 | 3/2007 |
| EP | 1776980 A1 | 4/2007 |
| EP | 1970091 A1 | 9/2008 |
| EP | 2272559 A1 | 1/2011 |
| FR | 2725902 A1 | 4/1996 |
| FR | 2752164 A1 | 2/1998 |
| GB | 906574 A | 9/1962 |
| GB | 2088215 A | 6/1982 |
| GB | 2230702 A | 10/1990 |
| GB | 2423267 A | 8/2006 |
| GB | 2450872 A | 1/2009 |
| JP | H03191965 A | 8/1991 |
| JP | H0751251 A | 2/1995 |
| JP | H08187286 A | 7/1996 |
| JP | H10179734 A | 7/1998 |
| JP | 2002028246 A | 1/2002 |
| RU | 2238111 C2 | 10/2004 |
| SU | 933100 A1 | 6/1982 |
| WO | WO-8101795 A1 | 7/1981 |
| WO | WO-8203558 A1 | 10/1982 |
| WO | WO-9204062 A1 | 3/1992 |
| WO | WO-9305840 A2 | 4/1993 |
| WO | WO-9311709 A1 | 6/1993 |
| WO | WO-9420160 A1 | 9/1994 |
| WO | WO-9519194 A1 | 7/1995 |
| WO | WO-9620021 A1 | 7/1996 |
| WO | WO-9632981 A1 | 10/1996 |
| WO | WO-9826835 A1 | 6/1998 |
| WO | WO-9833549 A1 | 8/1998 |
| WO | WO-9858693 A1 | 12/1998 |
| WO | WO-9907435 A1 | 2/1999 |
| WO | WO-9922789 A1 | 5/1999 |
| WO | WO-9933504 A1 | 7/1999 |
| WO | WO-0002614 A1 | 1/2000 |
| WO | WO-0003757 A1 | 1/2000 |
| WO | WO-0044324 A1 | 8/2000 |
| WO | WO-0112746 A1 | 2/2001 |
| WO | WO-0130419 A2 | 5/2001 |
| WO | WO-0168180 A1 | 9/2001 |
| WO | WO-0172353 A2 | 10/2001 |
| WO | WO-0193926 A2 | 12/2001 |
| WO | WO-0202165 A2 | 1/2002 |
| WO | WO-0207804 A1 | 1/2002 |
| WO | WO-0240083 A2 | 5/2002 |
| WO | WO-02053220 A2 | 7/2002 |
| WO | WO-02068014 A2 | 9/2002 |
| WO | WO-02081012 A2 | 10/2002 |
| WO | WO-02081013 A2 | 10/2002 |
| WO | WO-02083206 A2 | 10/2002 |
| WO | WO-02094352 A2 | 11/2002 |
| WO | WO-02100457 A2 | 12/2002 |
| WO | WO-02102442 A1 | 12/2002 |
| WO | WO-03015860 A1 | 2/2003 |
| WO | WO-03026728 A1 | 4/2003 |
| WO | WO-03068305 A1 | 8/2003 |
| WO | WO-03075980 A2 | 9/2003 |
| WO | WO-03095003 A1 | 11/2003 |
| WO | WO-2004012796 A1 | 2/2004 |
| WO | WO-2004026375 A1 | 4/2004 |
| WO | WO-2004029457 A1 | 4/2004 |
| WO | WO-2004030726 A1 | 4/2004 |
| WO | WO-2004037325 A1 | 5/2004 |
| WO | WO-2004054644 A1 | 7/2004 |
| WO | WO-2004056412 A2 | 7/2004 |
| WO | WO-2004064593 A2 | 8/2004 |
| WO | WO-2004071308 A1 | 8/2004 |
| WO | WO-2004087240 A1 | 10/2004 |
| WO | WO-2004098683 A1 | 11/2004 |
| WO | WO-2004101016 A1 | 11/2004 |
| WO | WO-2004101071 A2 | 11/2004 |
| WO | WO-2004110527 A1 | 12/2004 |
| WO | WO-2005002649 A1 | 1/2005 |
| WO | WO-2005004973 A1 | 1/2005 |
| WO | WO-2005018703 A2 | 3/2005 |
| WO | WO-2005037184 A2 | 4/2005 |
| WO | WO-2005037350 A2 | 4/2005 |
| WO | WO-2005039673 A2 | 5/2005 |
| WO | WO-2005046780 A1 | 5/2005 |
| WO | WO-2005065748 A1 | 7/2005 |
| WO | WO-2005068076 A1 | 7/2005 |
| WO | WO-2005072795 A2 | 8/2005 |
| WO | WO-2005092410 A1 | 10/2005 |
| WO | WO-2005094920 A1 | 10/2005 |
| WO | WO-2005118055 A1 | 12/2005 |
| WO | WO-2006003130 A1 | 1/2006 |
| WO | WO-2006015507 A2 | 2/2006 |
| WO | WO-2006015600 A2 | 2/2006 |
| WO | WO-2006024650 A2 | 3/2006 |
| WO | WO-2006032689 A1 | 3/2006 |
| WO | WO-2006032692 A1 | 3/2006 |
| WO | WO-2006061027 A2 | 6/2006 |
| WO | WO-2006061354 A1 | 6/2006 |
| WO | WO-2006062680 A1 | 6/2006 |
| WO | WO-2006062912 A1 | 6/2006 |
| WO | WO-2006075016 A1 | 7/2006 |
| WO | WO-2006077262 A1 | 7/2006 |
| WO | WO-2006077263 A1 | 7/2006 |
| WO | WO-2006089958 A1 | 8/2006 |
| WO | WO-2006097111 A2 | 9/2006 |
| WO | WO-2006108775 A2 | 10/2006 |
| WO | WO-2006120253 A2 | 11/2006 |
| WO | WO-2006121921 A2 | 11/2006 |
| WO | WO-2006122048 A1 | 11/2006 |
| WO | WO-2007000162 A2 | 1/2007 |
| WO | WO-2007002523 A2 | 1/2007 |
| WO | WO-2007020090 A1 | 2/2007 |

(56) References Cited

FOREIGN PATENT DOCUMENTS

| | | |
|---|---|---|
| WO | WO-2007065944 A1 | 6/2007 |
| WO | WO-2007071255 A1 | 6/2007 |
| WO | WO-2007071258 A1 | 6/2007 |
| WO | WO-2007093051 A1 | 8/2007 |
| WO | WO-2007093182 A2 | 8/2007 |
| WO | WO-2007122207 A1 | 11/2007 |
| WO | WO-2007140631 A1 | 12/2007 |
| WO | WO-2007140783 A2 | 12/2007 |
| WO | WO-2007140785 A1 | 12/2007 |
| WO | WO-2007141210 A1 | 12/2007 |
| WO | WO-2008014791 A1 | 2/2008 |
| WO | WO-2008014792 A1 | 2/2008 |
| WO | WO-2008048631 A1 | 4/2008 |
| WO | WO-2008052545 A1 | 5/2008 |
| WO | WO-2008065646 A1 | 6/2008 |
| WO | WO-2008092782 A1 | 8/2008 |
| WO | WO-2008092958 A2 | 8/2008 |
| WO | WO-2008092959 A1 | 8/2008 |
| WO | WO-2008135098 A1 | 11/2008 |
| WO | WO-2008148714 A1 | 12/2008 |
| WO | WO-2008155145 A1 | 12/2008 |
| WO | WO-2008155377 A1 | 12/2008 |
| WO | WO-2009004026 A1 | 1/2009 |
| WO | WO-2009007287 A1 | 1/2009 |
| WO | WO-2009010396 A1 | 1/2009 |
| WO | WO-2009010399 A1 | 1/2009 |
| WO | WO-2009016635 A2 | 2/2009 |
| WO | WO-2009098291 A1 | 8/2009 |
| WO | WO-2009098306 A1 | 8/2009 |
| WO | WO-2009101130 A1 | 8/2009 |
| WO | WO-2009101145 A1 | 8/2009 |
| WO | WO-2009103759 A1 | 8/2009 |
| WO | WO-2009106517 A1 | 9/2009 |
| WO | WO-2009144272 A1 | 12/2009 |
| WO | WO-2010003885 A1 | 1/2010 |
| WO | WO-2010003886 A1 | 1/2010 |
| WO | WO-2010034830 A1 | 4/2010 |
| WO | WO-2010072664 A1 | 7/2010 |
| WO | WO-2010112521 A1 | 10/2010 |
| WO | WO-2011012465 A1 | 2/2011 |
| WO | WO-2011015659 A1 | 2/2011 |
| WO | WO-2011121023 A1 | 10/2011 |

OTHER PUBLICATIONS

PCT/EP2008/054549 International Search Report completed May 30, 2008.
U.S. Appl. No. 12/665,278 Office Action dated Nov. 8, 2012.
U.S. Appl. No. 12/665278 Office Action dated Dec. 17, 2014.
U.S. Appl. No. 12/665,278 Office Action dated Feb. 25, 2014.
U.S. Appl. No. 12/665,278 Office Action dated Jul. 23, 2014.
U.S. Appl. No. 12/665,278 Office Action dated Jun. 18, 2013.
"Why inset®?" inset® infusion set product overview; http://web.archive.oro/web/20040906102448/http://www.infusion- set.com/Default.asOID=108; two pages.

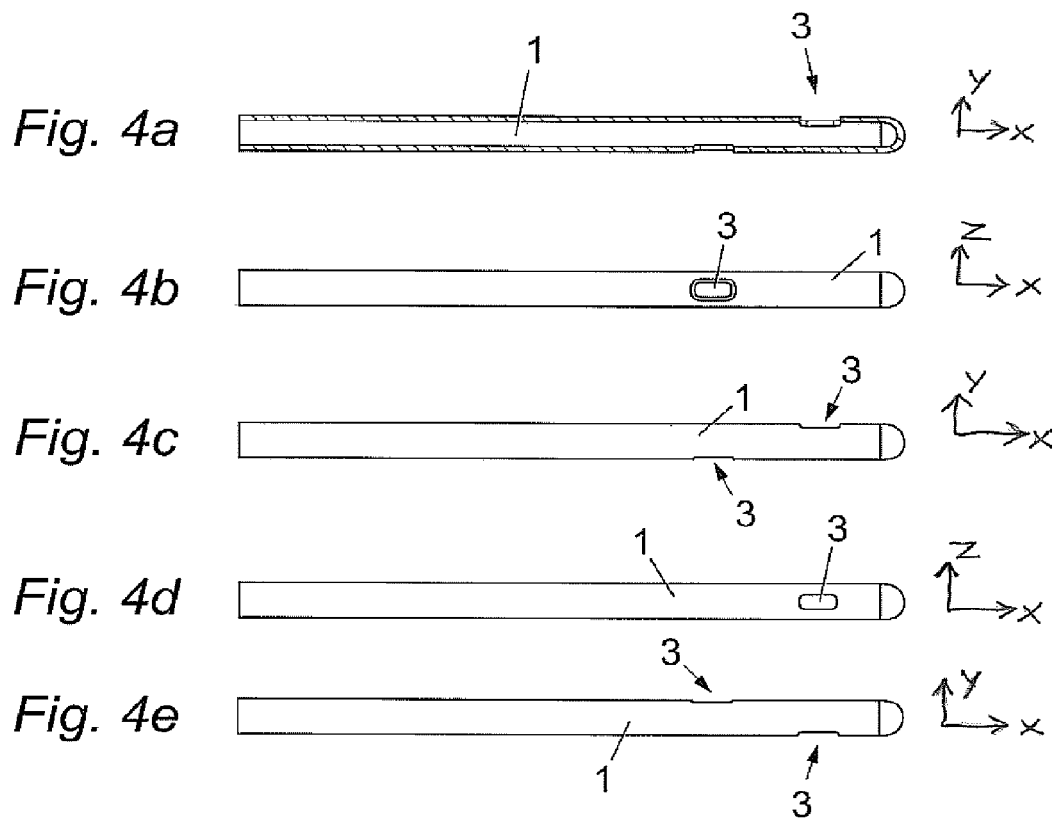
Fig. 4a
Fig. 4b
Fig. 4c
Fig. 4d
Fig. 4e
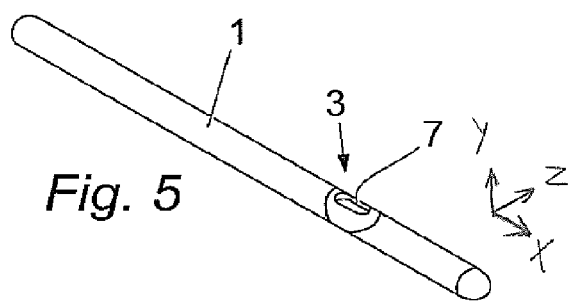
Fig. 5
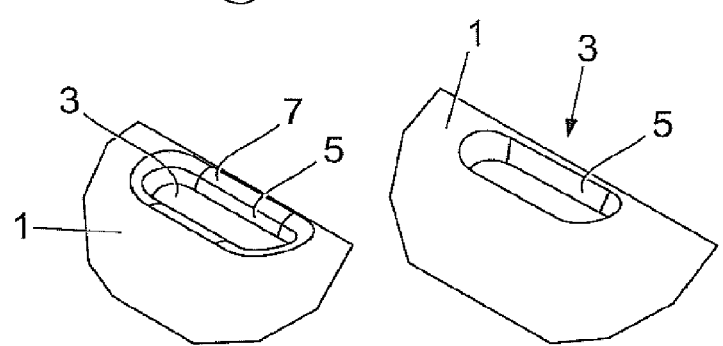
Fig. 7   Fig. 6

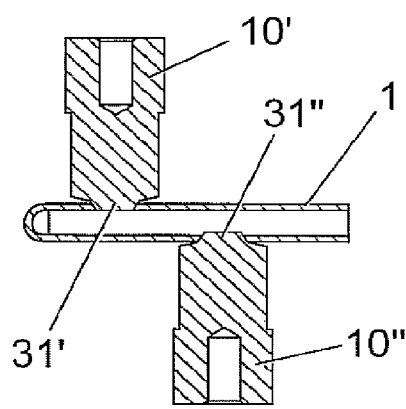
Fig. 13
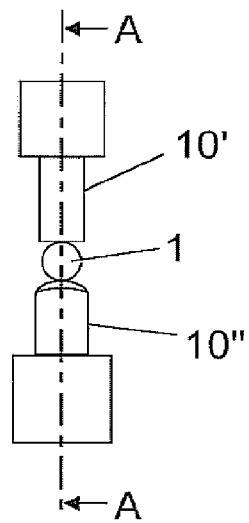
Fig. 12
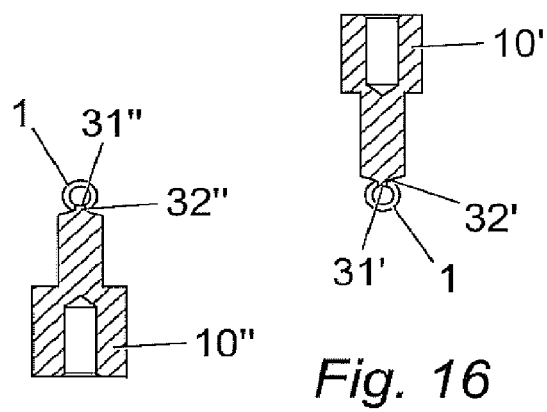
Fig. 15
Fig. 16
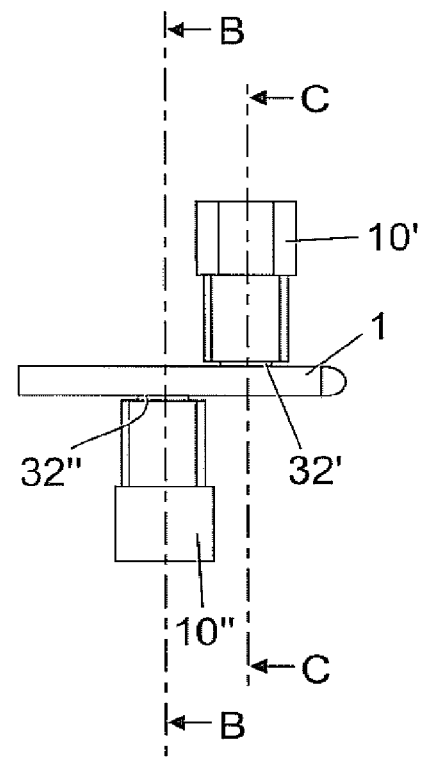
Fig. 14

APPARATUS FOR MAKING A CATHETER

CROSS-REFERENCE

This application is a divisional application of Ser. No. 12/665,278, filed Dec. 17, 2009, which claims the benefit under 35 U.S.C. §371 of International Application No. PCT/EP2008/054549, filed Apr. 15, 2008, which claims the benefit of European Application No. 07 012 017.5, filed Jun. 20, 2007, and U.S. Provisional Application Ser. No. 60/946,655, filed June 27, 2007 which are incorporated herein by reference in its entirety.

The present invention relates to a method of making a catheter for medical purposes, such as for insertion into a body opening for draining fluids, wherein the catheter comprises a flexible tube having a distal end region wherein the tube is provided with at least one draining opening. The invention further relates to an apparatus for performing such method.

A catheter includes a flexible tube with a distal end, which may be open or closed. The catheter is inserted into a body opening for draining fluids. In particular, the catheter may be a urinary catheter for insertion into a urinary pathway for collecting the fluids in this pathway.

In the distal end region of the catheter, the tube is provided with a number of openings for colleting fluid and draining the body opening, in particular the urinary pathway. A catheter of such kind is known from e.g. U.S. Pat. No. 5,919,170. As shown in this U.S. patent, the openings are preferably elongated to achieve a good fluid collecting capacity. These openings are usually punched into the tube. Examples of such catheters are known from e.g. GB-A-2 230 702 and U.S. Pat. No. 3,995,518.

U.S. Pat. No. 2,972,779 discloses two methods of providing the wall of a tubing of thermoplastic material with elongated holes having a smoothed outer edge. According to one method, the elongated holes are punched out and subsequently the edge is smoothed out in an operation whereby a moving grinding element, such as a rotating grinding wheel, is contacted with the sharp edge of the hole. According to another method, the elongated holes and their smooth edges are provided by punching and moulding by means of a metallic die having a punching element.

US 2005/0192560 A1 describes a method of providing a urology catheter by means of injection moulding. The catheter is provided with a drain eye in the wall of the tubing forming the body of the catheter. The inner and outer edges of the drain eye are smoothed out by forming radii between the wall of the drain eye and the inner and outer wall, respectively, of the tubing.

US 2004/0193143 A1 describes the forming of openings in a catheter by a punching operation. The openings may be rounded by a temperature treatment.

U.S. Pat. No. 4,259,276 describes a method of forming circular holes in thin plastic material. The method is exemplified by the forming of lateral holes in a cannula for epidural anaesthesia. Firstly, a needle is forced along its length through the wall of a nylon tubing to form a pierced aperture in the wall. The needle is withdrawn from the aperture, and drive is applied to the needle to rotate the needle at high speed about its longitudinal axis. The needle is then inserted into the pierced aperture without any drive being applied to the needle, so that contact of the rotating needle with the rim of the aperture produces frictional heating that serves to cause plastic flow smoothing out the contour of the pierced aperture around the needle.

GB 2 230 702 A describes injection moulding of a catheter having elongated holes with rounded ends.

The catheter must be carefully inserted and removed to avoid damaging the tissue of the pathway. This can be a problem with these known catheters, since the openings have a relatively sharp edge which can damage the soft tissue of the pathway when the catheter is moved longitudinally or rotated in the pathway during inserted or retracted. The catheters are usually produced in PVC or PUR so that a soft flexible tube is provided thereby reducing the risk of tissue damage. However, practical experience with the catheters have revealed that in particular tissue of a urinary pathway may nevertheless be damaged if the catheter is not carefully inserted or retracted from the pathway.

This problem is addressed by a method of making a catheter according to the present invention, wherein the catheter comprises a flexible tube having a distal end region wherein the tube is provided with at least one draining opening, wherein the peripheral edge on the outside of the tube is provided with a curvature for creating a smooth transition between the exterior surface of the tube and the substantially radially oriented cut constituting the opening side and wherein said curvature is a rounded edge with a curvature radius between 0.2-0.6 mm. By the invention, the opening in the tube is provided with a three-dimensional contour in a curved plane congruent with the curvature of the opening in the cylindrical surface of the tube. Hereby, a smooth catheter is provided where the risk of tissue damage is reduced.

The opening is preferably elongated with a longitudinal length substantially corresponding to the diameter of the tube. The catheter tube may be provided with different diameters so that different sizes of catheters may be provided. The drainage openings in the catheter tube are preferably provided with an angle between the opening side wall and the internal surface of the tube is within the range of 64-90°. This provides the catheter with good drainage properties as well as tissue preserving properties.

The catheter tube is made of a medical grade polymer preferably having a Shore A value in the range of approx. 64 to approx. 100, in particular the polymer may be a thermoplastic material, such as a polyester-type thermoplastic polyurethane (TPU) compound having a Shore A value of approx. 94±3, polyvinyichloride (PVC), preferably having a Shore A hardness ranging from 78 to 85, or polyurethane (PUR). By the invention, it is realised that a variety of materials are suitable for the catheter. For instance, the catheter tube may be of polyvinylchioride (PVC) with a hardness measured in Shore A with a value of 64 to 86, preferably 80 to 85 Shore A.

By the invention, there is also provided a method of making a catheter comprising a polymer tube with openings therein, said method for providing openings in a polymer tube of such catheter comprising the steps of:

providing a tube and punching at least one opening in the tube by advancing a cutting member in a substantially radial direction into the wall of the tube;

manipulating the outer peripheral edge region of the at least one opening by rounding the peripheral edge of the punched opening in the tube by advancing a heated forming member into the opening and thereby providing the edges of the opening with a shape corresponding to the shape of the distal end of the forming member, said forming member having a distal end adapted for engagement with an opening of the tube provided adjacent said distal end, wherein said distal end of the forming member is provided with a rounded shoulder transition at the foot of the distal end and with a protrusion extending from said shoulder transition region, said protrusion having a form fitting the opening in the tube, said rounded shoulder being formed with a contour in a curved plane congruent with the curvature of the opening in the cylindrical surface of the tube.

By finishing the opening in a separate after treatment process, the smooth curvature of the edge of the drainage opening is ensured.

In a preferred embodiment of the method, the loose cutaway material after the punching action is removed from the tube. Hereby, it is ensured that residues from the making of the opening do not drop into the inside of the catheter tube.

According to the invention there is also provided an apparatus for manipulating openings in a polymer tube for manufacturing a catheter, said apparatus comprising a movable frame comprising one or more forming stations, each forming station being adapted for receiving a flexible polymer tube with at least one opening, therein through the station and each forming station comprising a forming member, which is mounted in floating arrangement in said forming station, said forming member having a distal end adapted for engagement with an opening of the tube provided adjacent said distal end, wherein said distal end of the forming member is provided with a rounded shoulder transition at the foot of the distal end and with a protrusion extending from said shoulder transition region, said protrusion having a form fitting the opening in the tube, said rounded shoulder being formed with a three-dimensional contour congruent with the curvature of the opening in the cylindrical surface of the tube, and heating means for said forming member, so that said forming member may be heated to a temperature above the softening point of the polymer of the tube and preferably below the melting point of the polymer material of the tube.

In order to ensure a smooth result of the plastic deformation of the edge region of the opening in the tube, the distal end of the forming member is provided with a rounded shoulder transition at the foot of the distal end and with a protrusion extending from said shoulder transition region, said protrusion having a form fitting the opening in the tube, said rounded shoulder being formed with a three-dimensional contour congruent with the curvature of the opening in the cylindrical surface of the tube.

The rounded shoulder region is provided with a curvature radius between 0.2-0.6 mm and preferably the protrusion is elongated with a longitudinal length substantially corresponding to the axial extension of the opening on the tube.

In the preferred embodiment, the forming member is provided in a forming station which is arranged in a movable frame, and each forming station is adapted for receiving a flexible polymer tube through the station, and whereby the forming member is mounted in floating arrangement in a forming station, whereby the forming member is self-aligning when the protrusion is engaging the opening of the tube. This floating arrangement allows for inaccuracies in the positioning of the opening relative to the forming member.

The movable frame preferably comprises an upper section and a lower section where between the at least one forming station is arranged and the upper section is heated to a first temperature, such as 190°-200° C., and the lower section is heated to a second temperature, such as 170°-180° C., which is lower than the first temperature. The holding time of the forming member in contact with the tube is preferably 1 to 5 seconds, more preferably between 1.5 and 2.0 sec. Since there inherently is a heat loss between the movable frame and the shoulder and tip of the forming member, the temperatures applied to the upper and lower sections are somewhat higher than the. preferred temperature which is between the softening point of the polymer of the tube and below the melting point of the polymer material of the tube. This ensures that the deformation of the edge does not result in any deterioration of the surface texture and the material of the tube, e.g. burns or uncontrolled deformations. The forming member is made of metal, such as brass or similar heat resistant material that can withstand the applied heat. By the invention it is realised that the temperature may be even above the melting point of the tube material if the holding time is kept very low, such as below 1.5 seconds.

It is realised that the predetermined temperatures and the holding times are selected in accordance with the specific plastic material used for the tube.

In the following the invention is described with reference to some preferred embodiments shown in the accompanying drawings, in which.

Figure 8:
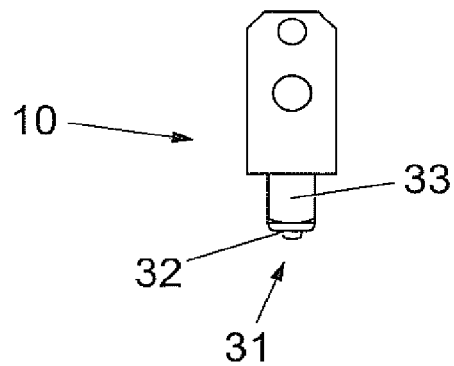
Figure 9:
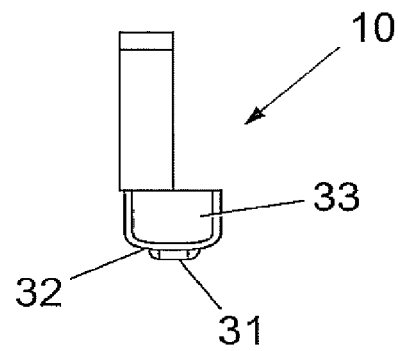
Figure 10:
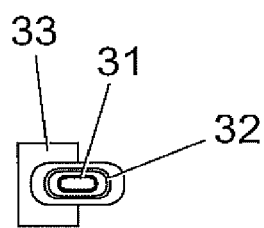
Figure 11:
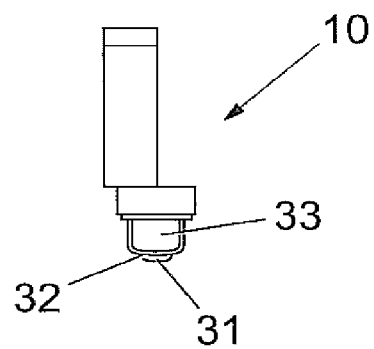

FIG. 4a)-e) are further views of a catheter according to the invention;

FIG. 5 is a perspective view of the catheter of FIG. 4;

FIG. 6 is a detailed perspective view of the opening after punching but before the rounding process according to the invention, FIG. 7 is the same as FIG. 6, but after the method of the invention is performed;

FIGS. 8-10 are three side views of a forming member in an apparatus for making the catheters according to a preferred embodiment of the invention;

FIG. 11 is a side view of a forming member of a smaller size than the forming member shown in FIG. 9;

FIG. 12 is a schematic end view along the catheter tube with two oppositely situated forming members in engagement in the draining openings;

FIG. 13 is a section view along A-A in FIG. 12;

FIG. 14 is a schematic side view of the catheter tube with two oppositely situated forming members in engagement in the draining openings;

FIG. 15 is a section view along B-B in FIG. 14;

FIG. 16 is a section view along C-C in FIGS. 14; and

Figure 17:
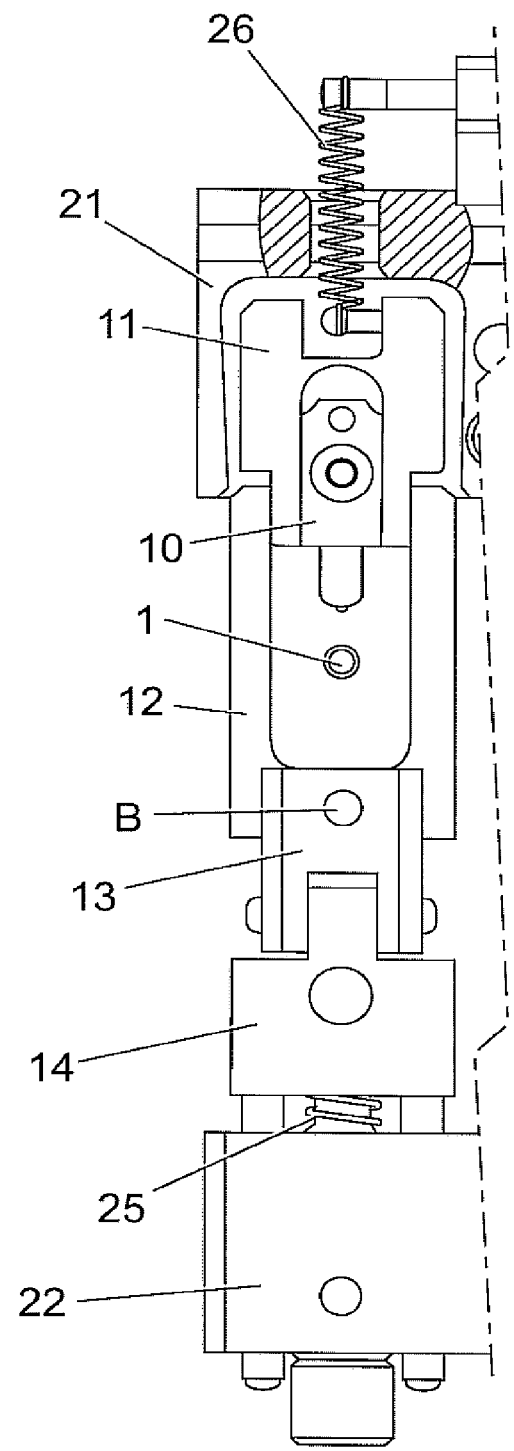
Figure 18:
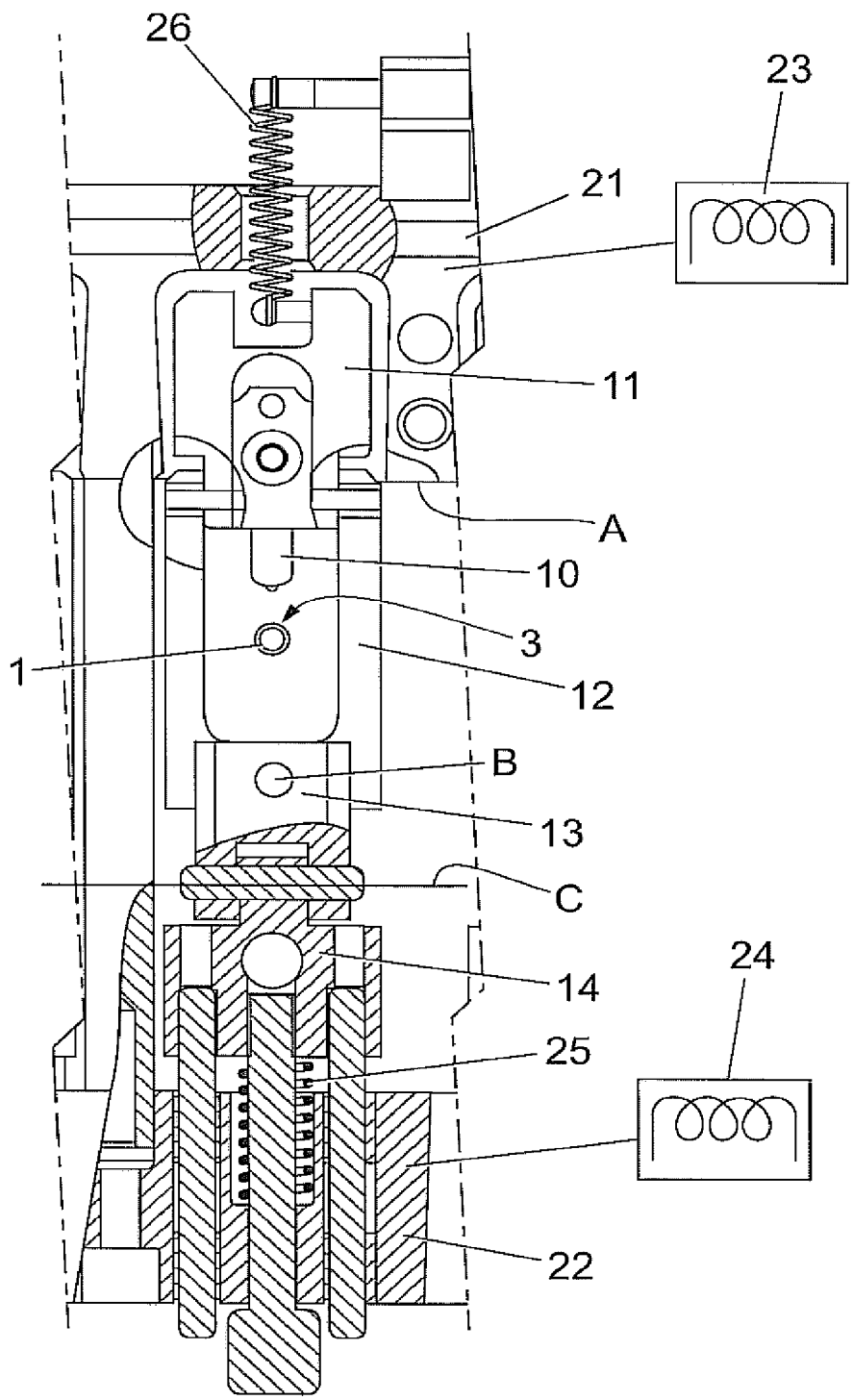
Figure 19:
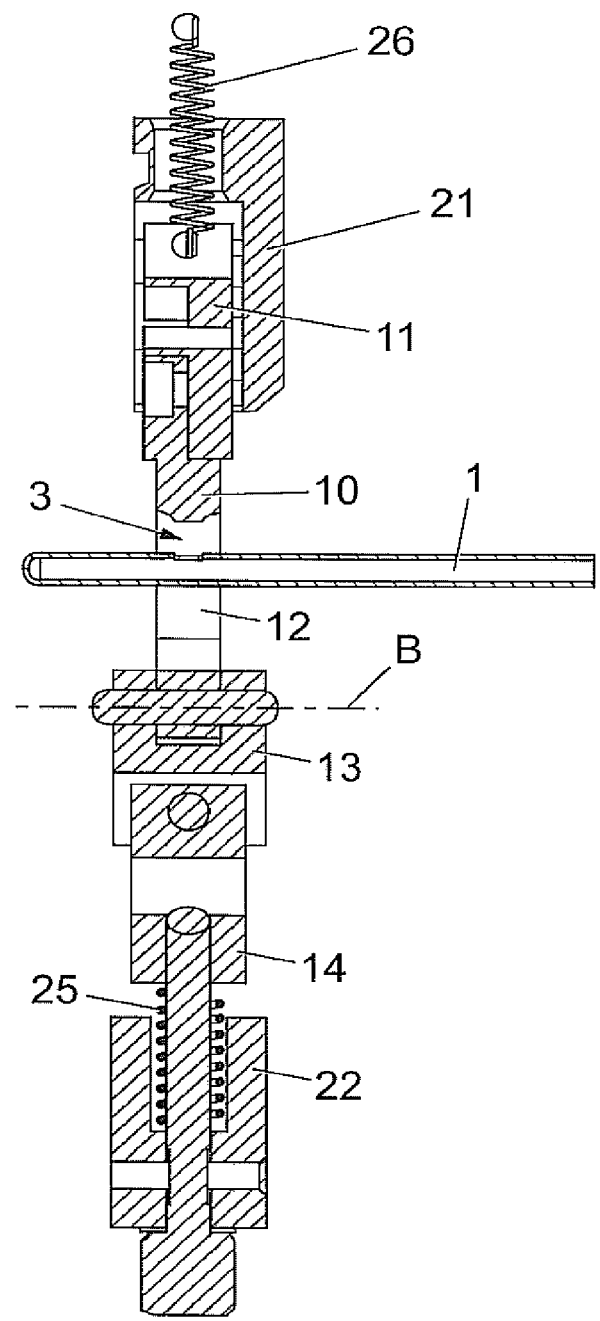
Figure 20:
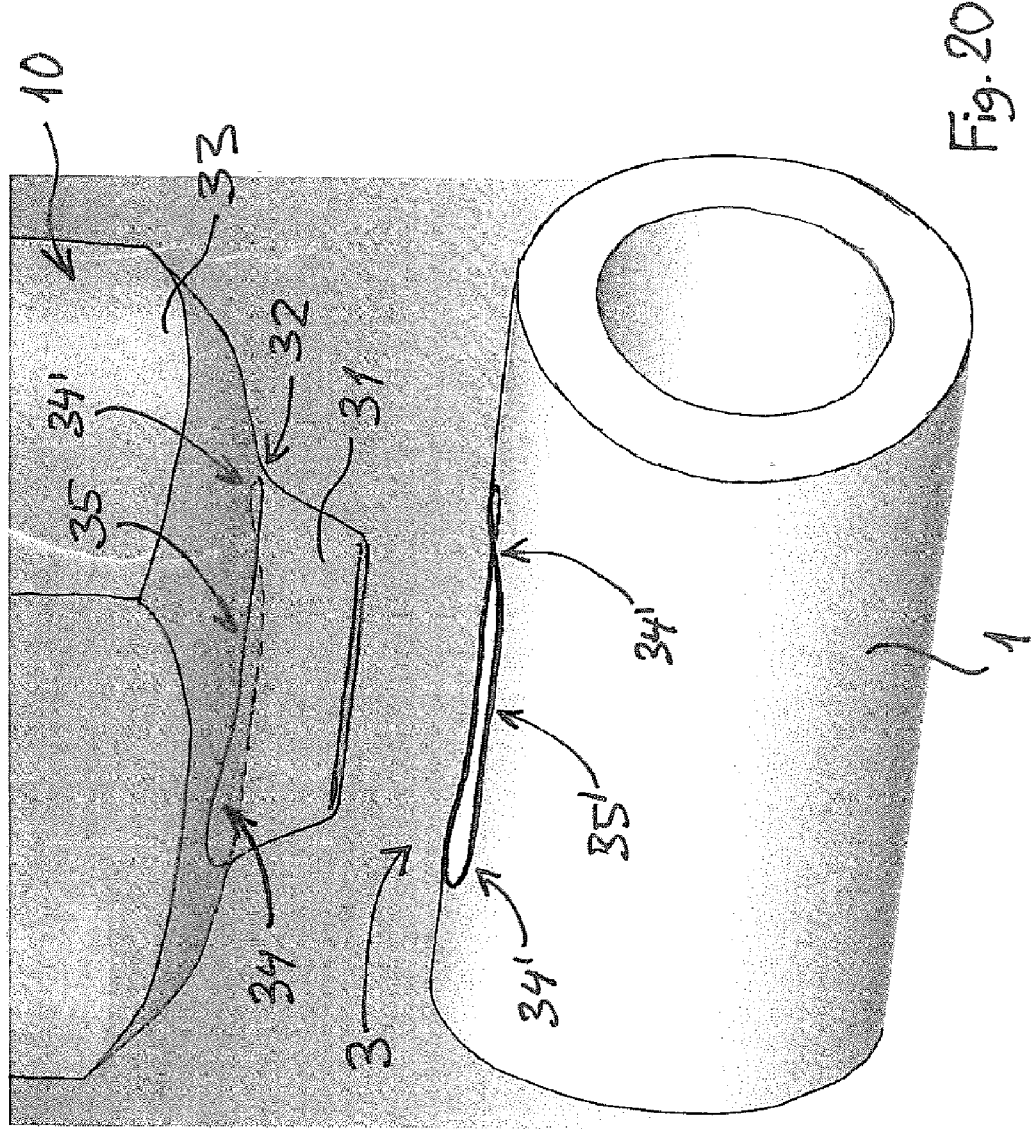

FIG. 17 is a schematic front view of a forming station in a moveable frame in an apparatus according to the invention;

FIG. 18 is a cross-sectional front view of the forming station in FIG. 17;

FIG. 19 is a cross-sectional side view of the forming station in FIG. 17; and FIG. 20 is a detailed perspective view of the geometry of the distal end of the forming member and the opening in the tube.

With reference to FIGS. 1 to 5, a catheter according to the invention comprises a flexible tube 1, which is made of a plastic material, preferably polyvinylchloride (PVC) or polyurethane (PUR) and attached to a connector 2. The tube 1 is provided with a number of openings 3 in region of the distal end 4 of the tube 1. This opening 3 serves a drain for collecting fluids outside the tube to flow inside the catheter tube 1 for draining the body space in which the catheter is inserted. The opening 3 has a generally radially oriented side wall 5 (see FIG. 3), and which may be provided with an angular orientation v of between 60-90' relative to the inner surface of the wall of the tube 1 (see FIG. 2). The opening .3 may involve a slight indentation 6 into the tube inner space. This indentation 6 may be between 0-0.5 mm. The hole 3 is provided with rounded external edges 7, so that a smooth transition between the opening walls 3 and the surface of the tube 1 is ensured.

The openings 3 are punched in the tube using a punching tool (not shown) or other cutting tool. After the opening 3 is cut in the cutting process, the loose tube wall section is removed leaving an opening in the tube 1 where the opening 3 has a sharp outer edge, as shown in FIG. 6. By the finishing process according to the invention, the outer edge is rounded as shown in FIG. 5 and FIG. 7.

For providing the rounded edge 7 on the opening 3, a moveable frame 20 is used; see FIGS. 17 to 19. The moveable frame includes one or more forming stations, where each forming station is adapted for receiving a flexible polymer tube 1 through the station adjacent a forming member 10. The forming station further includes a holding member 11 to which the forming member 10 is fixed. This member is connected to an upper section 21 of the frame 20 by a spring arrangement 26. The holding member 11 is furthermore pivotably connected to the distal ends of a fork-like member 12, so that the fork-like member 12 and the holding member 11 may pivot relative to each other about an axis A substantially perpendicular to the tube 1 above the tube 1. The fork-like member 12 is at its base pivotably connected to a third member 13, where the two members 12, 13 may pivot about an axis B substantially parallel to the tube 1 below the tube 1. This third member 13 is then pivotably connected to a lower member 14 allowing these members 13, 14 to pivot about an axis C substantially perpendicular to the tube 1. This lower member 14 is preferably vertically slidably secured to a lower section 22 of the frame via a spring 25. When the frame 20 is moved relative to the tube 1, the forming member 10 is moved in engagement with the opening 3 in the tube 1. By the pivoting arrangements, the forming member 10 is floatingly arranged in the frame whereby the forming member 10 may be self-centering in the opening 3.

With reference to the FIGS. 8-10 and 11, the forming member 10 has a distal end 33 adapted for engagement with the opening 3 of the tube 1 provided adjacent the distal end 33. The distal end 33 of the forming member 10 is provided with a rounded shoulder transition 32 at the foot of the distal end 33 and with a protrusion 31 extending from the shoulder transition region 32. The protrusion 31 has a form fitting the opening 3 in the tube 1. The rounded shoulder 32 is formed with a three-dimensional contour congruent with the curvature of the opening 3 in the cylindrical surface of the tube 1. It is important to realise that the edge 7 of the opening on the tube 1 extend in a curved plane, i.e. the edge 7 has a three-dimensional extension. As shown in FIGS. 9 and 11, the forming member 10 may be provided with different distal ends in order to adapt a forming member to a specific tube and opening size.

By applying heat to the frame and thereby to the members in the forming station, which are all made of a thermally conductive material, preferably steel or similar metal, the forming member 10, which is made of brass or the like, is heated to a temperature above the softening point of the polymer of the tube and preferably below the melting point of the polymer material of the tube. A first heat source 23 is applying heat to the upper section 21 of the frame 20 and a second heat source 24 is applying heat to the lower section 22 of the frame 20. The first temperature may preferably be between 180-200° C.±10° C. and the second temperature may be between 170-190° C.±10° C. The diameter of the tube may be between 2.0-6.0 mm and the temperature applied is preferably in the lower range of the temperature range if the diameter is small. The temperature ranges as well as the holding times may vary depending on the type of material and the thickness of the tube wall as well as the diameter of the tube.

When heat is applied to the forming station and thereby to the forming member 10 the forming member 10 is advanced into engagement with the opening 3 in the tube 1 for a predetermined period of time, preferably between 1.5-2.0 seconds. The temperatures applied and the times of engagement, i.e. the holding time, are selected in accordance with the tube material and the tube dimensions. The temperature may be even above the melting point of the tube material if the holding time is kept very low. Hereby, the edge 7 is rounded in a plastic deformation process as the heated forming member 10 is moved into engagement in the opening 3. The protrusion 31 fits into the opening 3 and as the protrusion aligns in the opening 3, the rounded transition 32 thereby advances correctly towards the edge region and thereby creates the desired rounding of the edge 7. The floating arrangement described earlier facilitates the alignment of the forming member 10 in the opening.

As shown in FIGS. 12 to 16, two openings in a catheter made can be processed simultaneously by having two movable frames (not shown) adjacent each other so that a first forming member 10' is advanced into contact with an opening from a first side of the tube and a second forming member 10" is advanced into contact from a side opposite the first side.

Figure 1:
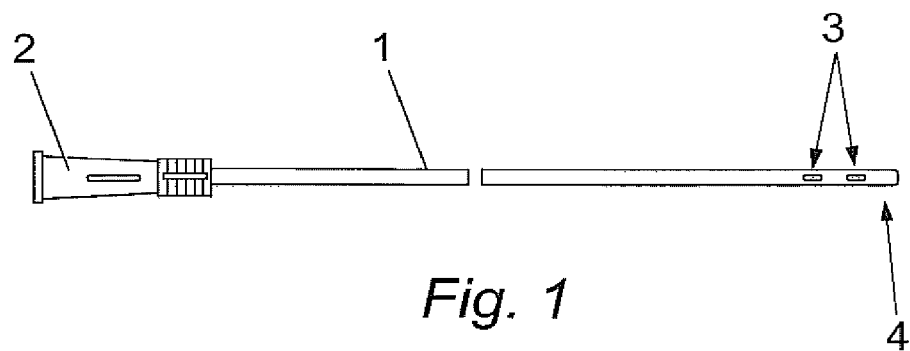
FIG. 1 is a side view of a catheter of the kind the present invention concerns.
Figure 2:
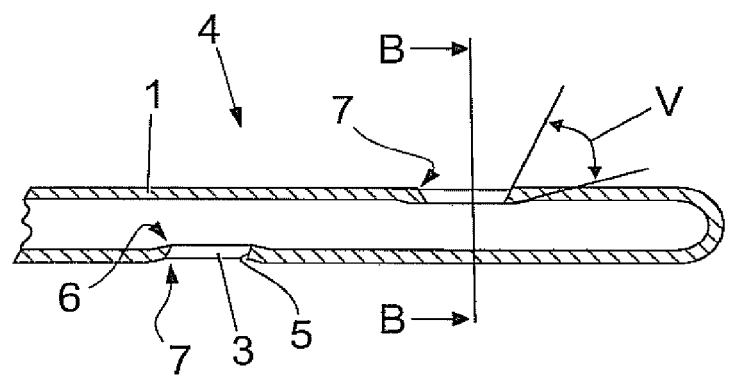
FIG. 2 is a detailed view of an axial cross-section of the tip of a catheter according to the invention.
Figure 3:
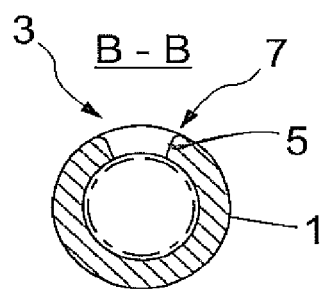
FIG. 3 is a detailed view of a radial cross-section of the tip of a catheter according to the invention through the section B-B in FIG. 2.

The form of the edge 7 of the opening 3 in the tube 1 is determined by the geometry of the distal end of the forming member 10, in particular the shoulder transition 32 but also the protrusion 31. The resulting tube opening 3 may be provided with an inclined side surface 5 with an angle v between 60°-90° in the axial direction between the opening side and the inner surface of the tube 1, see FIG. 2. As shown in FIG. 3, the side walls 5 of the opening 3 may have a radial direction in the cross-sectional direction. Moreover, a slight inwardly extending indentation 6 having a radial extension between 0-0.48 mm is also provided in the tube.

EXAMPLES

For different diameter sizes, tests have been made for finding a suitable relationship between temperature, holding time and pressure of the forming member 10. In practice, the pressure may be predetermined as the insertion depth of the distal end of the forming member 10 and may be controlled in relation to the predetermined measurements and tolerances. By testing, the chosen combinations of temperature and time listed in table 1 below are found stabile for manufacturing and optimal with respect to minimizing the process time.

The parameters for the tests were:

The tube material was ESTANE 58212 TPU which is a thermoplastic polyurethane compound with a glass transition temperature of −25° C., an extrusion temperature of 200-210° C. and an injection moulding temperature of 195-205° C.

The shape and the temperature of the distal end of the forming member.

The time the forming member is making contact with the tube.

The insertion depth of the distal end of the forming member in the tube, referred to as pressure).

TABLE 1

| ESTANE ® 58212 TPU | | |
|---|---|---|
| Diameter size | Temp. | Time |
| CH08 | 170° C. | 1.5 s |
| CH10 | 180° C. | 1.7 s |
| CH12 | 180° C. | 1.7 s |
| CH14 | 180° C. | 1.7 s |
| CH16 | 180° C. | 1.7 s |
| CH18 | 180° C. | 2.0 s |

Compared to the parameters in table 1, by lower temperatures or shorter time or lower pressure (i.e. shorter insert distance)

it was found that the rounding was not complete and/or the deformation was not permanent.

Compared to the parameters in table 1, by larger temperatures, the material became too liquidized and melted and by longer time or larger pressure resulted in elevated edges in the transition between the tube and the forming member 10.

In relation to the geometric shape of the distal end of the forming member 10 it was found of imperative importance that the rounding of the edge is a stamp of the forming member by a certain deformation of the tube. Accordingly, the shape of the distal end of the forming member is of most importance for obtaining a satisfactory rounding of the edge of the catheter opening 3. By matching the three-dimensional contour of the edge on the tube when shaping the distal end of the forming member, i.e. with the same dimensions, rounding and sizes, a satisfactory result was considered achieved. Moreover, by forming the distal end of the forming member with appropriate angles and transitions it was found further ensured that no "sharp" edges would occur on the tube.

As indicated in FIG. 20, the contour of the shoulder transition portion 32 of the distal end 33 of the forming member 10 are shaped with two end sections 34 with a "straight" section 35 there between. The corresponding edge contours are marked on the tube opening 3 by 34' and 35', respectively. Whereas the straight section 35 is substantially in the same plane, due to the cylindrical shape of the tube and the central straight shape of the opening when viewed from the Y-axis, the ends 34, 34' are curved out of this plane because of the rounded, semi-circular end portions of the opening again when viewed from the Y-axis. This three-dimensional shape of the distal end of the forming member 10 is found particularly advantageous in order to achieve an opening 3 with an entirely and truly smooth contour.

This geometry ensures that an unacceptable deformation on the inside of the tube is prevented.

The resulting rounded edge along the opening in the catheter tube is in an X-Y and/or Y-Z plane. When viewing the catheter in the Z-direction, such as shown in FIG. 2, FIGS. 4b and 4e, it becomes apparent that the contour of the edge of the opening 3 is curved in an X-Y plane perpendicular to the rounded edge plane at any given place on along the opening. This curvature of the side contour of the opening is due to the cylindrical form of the tube. This in turn means that when the opening is cut the central section, i.e. the straight section 35' in FIG. 20, becomes lower that the outer contour of the tube view viewed from the side, e.g. as schematically shown in FIGS. 4a, 4c and 4e. The end sections of the opening, i.e. the extremes in the X direction of the opening, curve outwards towards the straight outer contour of the tube itself. By the invention it is realised that it is important to acknowledge and pay attention to this geometric shape when forming the rounded edges on the opening in order to avoid sharp edges and to ensure a truly smooth transition between the outer surface of the cylindrical tube and the inner side wall 5 of the opening 3.

Above, the invention and the different aspects thereof are described with reference to some preferred embodiment. However, by the invention it is realised that other variations and equivalent solutions may be provided without departing from the scope of the invention as defined in the accompanying claims, such as other suitable materials and other process parameters, such as temperature and time, may be chosen in order to achieve a satisfactory result when using tubes in a predetermined material.

The catheter according to the invention may be a urinary catheter, a tracheostomy catheter or any other type of catheters for insertion into a body cavity for draining fluids.

What is claimed is:

1. A method of making a catheter comprising a polymer tube with openings therein, said method comprising:
providing a tube and punching at least one opening in the tube by advancing a cutting member in a substantially radial direction into the wall of the tube and providing the at least one opening with a three-dimensional edge contour, whereby central, straight sections of the edge contour of the opening become lower than the outer contour of the tube when the tube is viewed from the side, and end sections of the edge contour of the opening curve outwards towards the straight outer contour of the tube itself;
manipulating an outer peripheral edge region of the at least one opening by rounding the peripheral edge of the punched opening in the tube by advancing a heated forming member a predetermined distance into the opening and providing the peripheral edges of the opening with a shape corresponding to a shape of a distal end of the forming member, said distal end of the forming member is provided with a rounded shoulder transition portion at a foot of the distal end and with a protrusion extending from said shoulder transition region, said protrusion having a form fitting the opening in the tube, said distal end of the forming member being shaped so that it matches the three-dimensional contour of the edge of the punched opening in the tube, a contour of the shoulder transition portion of the distal end of the forming member is shaped with two end sections with substantially straight sections therebetween, corresponding to the end sections and the central straight sections of the edge contour of the opening, respectively, the substantially straight sections of the contour of the shoulder transition portion extend substantially in the same plane, the end sections of the contour of the shoulder transition portion curve out of said plane;
holding said heated forming member in said advanced position for a predetermined holding time; and
retracting the forming member.

2. A method according to claim 1, further comprising removing loose cut-away material after the punching action.

3. A method according to claim 1, further comprising providing the forming member in a forming station positioned in a movable frame, the forming member is mounted in floating arrangement in the forming station, the forming member is self-aligning when the protrusion is engaging the opening of the tube received in the forming station.

4. A method according to, claim 1, comprising heating an upper section of the movable frame to a first temperature and heating a lower-section of the movable frame to a second temperature with the forming station between the upper section and the lower section, wherein the second temperature is lower than the first temperature.

5. A method according to claim 1, comprising providing the distal end of the forming member with a rounded shoulder transition with a curvature radius between about 0.2-0.6 mm at the foot of the distal end and with a protrusion extending from said shoulder transition region which is inserted into the opening of the tube, and providing the protrusion is provided with a form fitting the opening in the tube, and forming the rounded shoulder with a three-dimensional contour congruent with the curvature of the opening in the cylindrical surface of the tube.

6. A method according to claim 1, comprising providing the tube made of a medical grade polymer having a Shore A value in the range of about 64 to about 100, and heating the forming member to a temperature above the softening point of the polymer of the tube and below the melting point of said polymer.

7. A method according to claim 1 wherein the predetermined holding time is about 1 to 5 seconds.

* * * * *